United States Patent [19]

Schelbeck

[11] Plant 5,179

[45] Jan. 17, 1984

[54] BEGONIA PLANT NAMED BARBARA

[75] Inventor: Erland V. Schelbeck, Odense, Denmark

[73] Assignee: L. Daehnfeldt Ltd., Odense, Denmark

[21] Appl. No.: 420,498

[22] Filed: Sep. 20, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A begonia plant named Barbara having large double compound bright pink flowers contrasting with dark green firm glabrous foliage; vigorous in growth habit, and easily manipulated for year round flower production, especially for larger containers and hanging baskets for interior decorating without flower fading under abnormal conditions.

1 Drawing Figure

1

The present invention related to a new and distinct cultivar of begonia plant, botanically known as *hiemalis begonia* (Fotsch), and referred to by the cultivar name Barbara.

The new cultivar was discovered by me as a seedling from a controlled crossing of tuberous seedling P-183 as the seed parent with begonia Socotrana as the pollen parent. Asexual reproduction by stem and leaf cuttings has reproduced the unique features of the new cultivar through successive propagations.

The following characteristics distinguish the new begonia from both its parents and other begonias commercially known and used in the floriculture industry:

1. My new cultivar shows no pubescense on the foliage as does the tuberous seed parent. The plant form, though as vigorous as the seed parent, is more compact and sturdier.

2. In comparison to the pollen parent which has light pink single open face flowers, the new cultivar is double with many flowers having 2–3 and sometimes four whorls of tepals in the center of the flower, as illustrated.

3. A most outstanding feature of Barbara is the bright shade of pink tepals that maintain the same tone from opening until flower drop even under high light levels. The flowers seldom appear to be old.

4. The new cultivar is considered to be highly floriferous. The stems on which flowering occurs tend to have initiation and development at several nodes at one time.

5. The keeping qualities of the flowers and the foliage in all seasons allows production and sales efficiencies to be maximized.

6. The new cultivar tends to be very vigorous so that 10 cm. pot production is best done with shoot cuttings and tip pinching.

7. Propagation by leaf cuttings is difficult under light and high temperatures in summer months. Stem cuttings can readily be produced in this season.

8. Barbara is very superior with respect to color and keeping qualities of winter crops of hiemalis begonias. Indoor hanging baskets for holidays will have a new potential.

The accompanying colored photograph taken June 1982 illustrates in perspective the overall appearance of Barbara grown from a leaf cutting in a 15 cm. plastic

2 pot, and showing the colors as true as it is reasonably possible to obtain in a colored reproduction of this type.

The following is a detailed description of my new begonia cultivar based on plants produced under commercial practices in Odense, Denmark, and Ashtabula, Ohio Color references are made to the Royal Horticultural Society Colour Chart except where general color terms of ordinary dictionary significance are used.

Parentage:

A controlled crossing of my tuberous seedling P-183 with the species begonia Socotrana.

Propagation:

(A) *Type cutting.*—Stem cutting.

(B) *Time to root for planting.*—27–30 days at 21° C. summer; 25–28 days at 21° C. winter.

(C) *Rooting habit.*—Uniform, dendritic, fibrous.

(D) *Time for shoot development.*—70–85 days to develop adventitious shoots 5–6 cm. long from stick date.

Plant description:

(A) *Form.*—Low bush type, self branching, herbaceous.

(B) *Habit of growth.*—Generally rapid, vigorous with strong stems, strong peduncles, and strong pedicels.

(C) *Foliage.*—Leaves simple, alternate; borne on vigorous petioles; firm. (1) Size: Average leaf at maturity from 10–12 cm. long. Leaves may be larger or smaller depending on density of leaf canopy. (2) Shape: Ovate, slightly concave. (3) Texture: Leaf is firm, top glabrous, underside rugose. (4) Margin: Crenate. (5) Color: Young foliage top side, green 137D, underside, yellow green 146D; mature foliage top side, yellow green 147A to green 139; underside, yellow green 147C to 148A. (6) Venation: Palmate.

Flowering description:

(A) *Flowering habits.*—Flowering in racemes, with several clusters arising from the stem nodes at same time giving a highly floriferous appearance. Flowering is continuous for long periods of time.

(B) *Natural flowering season.*—Flowering occurs naturally with shortened day lengths beginning mid-September and continuing through May.

Reducing day length in summer speeds up flower initiation.

(C) *Flower bud description.*—Flat, round, very light pink, progressively deepening in color until tepals begin to open.

(D) *Flowers borne.*—On vigorous peduncles and pedicels in a raceme. The extra doubleness of the flowers causes a pendulous appearance because of the weight of the flowers.

(E) *Quantity.*—Very floriferous, often having 18–20 flowers per main stem in flowering stage at one time.

(F) *Tepals.*—(1) Shape: Nearly circular. (2) Color, top side in winter when opening, red purple 68B to red purple 73B. Color tone is brighter than either, very little fading at any time; under side, starts red purple 68D, darkening to 73B. (3)

Number of tepals: From 16 to 32. (4) Size of tepals: 4 basal tepals 25–30 mm.; interior tepals 10–20 mm. (5) Flower size: Up to 5 cm. in diameter.

(G) *Reproductive organs.*—Sterile triploid hybrid.

Disease resistance:

No particular increase in resistance to diseases observed to date.

I claim:

1. A new and distinct begonia cultivar named Barbara, as described and illustrated, and particularly characterized by its vigorous, compact growth habit; bright pink tepals that maintain color even under high light conditions; floriferous habit, and by its excellent keeping qualities.

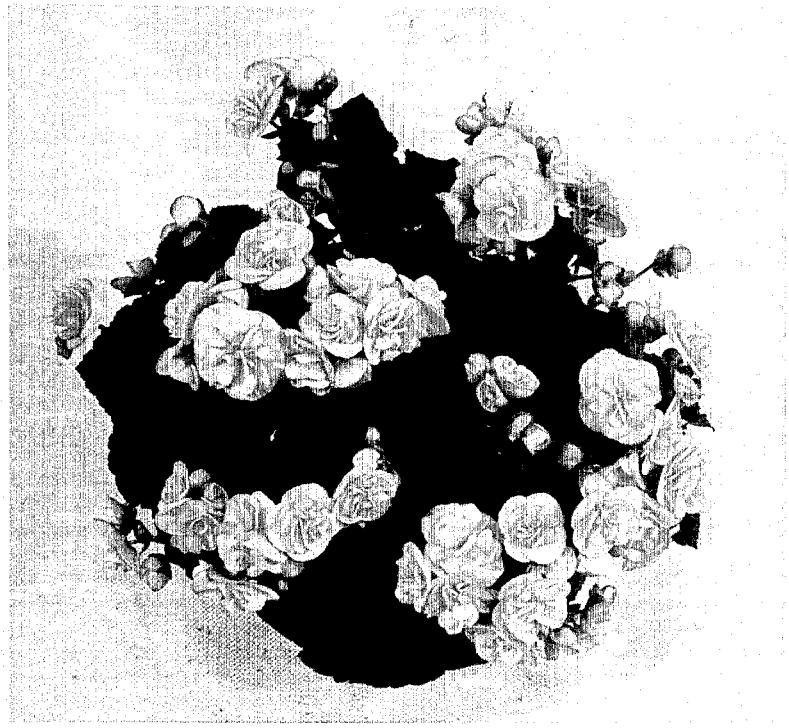

* * * * *